(12) United States Patent
Berberich

(10) Patent No.: US 9,176,036 B2
(45) Date of Patent: Nov. 3, 2015

(54) APPARATUS FOR HANDLING SPECIMEN SLIDES HAVING SELECTABLY RECEIVABLE GLASS OR TAPE COVERSLIPPING MODULES

(71) Applicant: Leica Biosystems Nussloch GmbH, Nussloch (DE)

(72) Inventor: Markus Berberich, Heidelberg (DE)

(73) Assignee: LEICA BIOSYSTEMS NUSSLOCH GMBH, Nussloch (DE)

( * ) Notice: Subject to any disclaimer, the term of this patent is extended or adjusted under 35 U.S.C. 154(b) by 0 days.

(21) Appl. No.: 14/265,496

(22) Filed: Apr. 30, 2014

(65) Prior Publication Data

US 2014/0348725 A1    Nov. 27, 2014

(30) Foreign Application Priority Data

May 22, 2013  (DE) .......................... 10 2013 105 220

(51) Int. Cl.
*A61B 10/00*   (2006.01)
*G01N 1/36*    (2006.01)
*G01N 35/00*   (2006.01)

(52) U.S. Cl.
CPC ............ *G01N 1/36* (2013.01); *G01N 35/00029* (2013.01); *G01N 2035/00079* (2013.01); *G01N 2035/00138* (2013.01)

(58) Field of Classification Search
CPC ...................... G01N 2035/00881; A61B 10/00
See application file for complete search history.

(56) References Cited

U.S. PATENT DOCUMENTS 6,821,072 B2 *  11/2004  Thiem et al. .................. 414/268
8,709,360 B2 *  4/2014   Hajrovic et al. .............. 422/536
2012/0287261 A1  11/2012  Neef et al.
2012/0290127 A1  11/2012  Neef et al.

FOREIGN PATENT DOCUMENTS

EP          1860422 A1    11/2007

* cited by examiner

*Primary Examiner* — Jyoti Nagpaul
(74) *Attorney, Agent, or Firm* — Hodgson Russ LLP

(57) ABSTRACT

An apparatus (10) for handling specimen slides comprises a first module receiving region (18) in which a coverslipping module (100, 200), for coverslipping thin sections arranged on the specimen slides with a coverslipping medium and a coverslipping element, is receivable. A first electrical interface is provided in the first module receiving region (18) for attachment of a coverslipping module (100, 200), this interface being embodied so that by way of it, both a glass coverslipping module (100) for coverslipping with glass wafers and a tape coverslipping module (200) for coverslipping with tapes is attachable. The first module receiving region (18) is furthermore embodied in such a way that a tape coverslipping module (200) or a glass coverslipping module (100) is selectably receivable in it.

12 Claims, 7 Drawing Sheets

APPARATUS FOR HANDLING SPECIMEN SLIDES HAVING SELECTABLY RECEIVABLE GLASS OR TAPE COVERSLIPPING MODULES

CROSS REFERENCE TO RELATED APPLICATIONS

This application claims priority of German patent application number 10 2013 105 220.7 filed May 22, 2013, the entire disclosure of which is incorporated by reference herein.

FIELD OF THE INVENTION

The invention relates to an apparatus for handling specimen slides which encompasses at least one first module receiving region in which a coverslipping module, for coverslipping thin sections arranged on the specimen slides with a coverslipping medium and a coverslipping element, is receivable.

BACKGROUND OF THE INVENTION

For microscopic investigations, the samples to be investigated are cut with the aid of microtomes into very thin slices called "thin sections." The thin sections are then placed onto specimen slides and are coverslipped, using coverslipping machines, with a coverslipping medium and a coverslipping element; once the coverslipping medium is dry, they can then be conveyed to a microscope for microscopy. The coverslipping elements used here are on the one hand glass coverslips in the form of thin glass wafers, or alternatively tapes.

The handling of glass wafers and of tapes in the context of coverslipping is fundamentally different, so that correspondingly different coverslipping modules must be used therefor. With known coverslipping machines the customer must decide, upon purchase, whether he or she wishes to have a coverslipping machine for coverslipping with glass wafers, or a coverslipping machine for coverslipping with tapes. With many machines, subsequent conversion is not possible at all or requires considerable outlay, since the coverslipping machine must be sent for that purpose to the manufacturing company's customer service department, which must laboriously rebuild it.

SUMMARY OF THE INVENTION

The object of the invention is to describe an apparatus for handling specimen slides that enables the greatest possible variability when coverslipping thin sections arranged on specimen slides.

This object is achieved by an apparatus having the features of claim 1. Advantageous refinements of the invention are described in the dependent claims.

According to the present invention, a first electrical interface is provided in the first module receiving region for attachment of a coverslipping module, this first electrical interface being embodied so that by way of it, both a glass coverslipping module for coverslipping specimen slides with glass wafers and a tape coverslipping module for coverslipping specimen slides with tapes can be attached. In addition, the module receiving region is also mechanically embodied in such a way that a tape coverslipping module or a glass coverslipping module is selectably receivable in it. As a result of the modular construction, a tape coverslipping module can thus be exchanged at any time for a glass coverslipping module, or vice versa, by the customer him- or herself, so that the customer no longer requires two separate devices but instead can easily convert an existing device by exchanging the corresponding modules. This offers simple handling and maximum flexibility for the customer.

The glass coverslipping modules and the tape coverslipping modules are, in particular, dimensioned in such a way that they have the same dimensions. In particular, at least those regions which come into contact with the elements demarcating the module receiving region are of identical configuration, so that it is easily possible to insert both types of coverslipping module into the first module receiving region. Thanks to the use of an identical interface for both types of coverslipping module, the latter can easily be exchanged.

In the context of this Application, the term "coverslipping module" is to be understood in particular to mean both a tape coverslipping module and a glass coverslipping module, unless one of these two types of coverslipping module is explicitly indicated. The term "types of coverslipping module" is understood in particular to mean that there are two types of coverslipping module, namely glass coverslipping modules and tape coverslipping modules.

In a particularly preferred embodiment of the invention the apparatus encompasses a second module receiving region for receiving a coverslipping module for coverslipping thin sections arranged on specimen slides with a coverslipping medium and a coverslipping element. A second electrical interface for attachment of a coverslipping module is provided in the second receiving region, this second electrical interface being embodied so that by way of it, both a glass coverslipping module for coverslipping specimen slides with glass wafers and a tape coverslipping module for coverslipping specimen slides with tapes can be attached. In addition, the second module receiving region is also embodied in such a way that both a tape coverslipping module and a glass coverslipping module are receivable in it. The result of providing the module receiving regions is that two coverslipping modules can be accommodated in only one apparatus, and a high throughput can thus be achieved. For example, a tape coverslipping module can be arranged in one of the module receiving regions and a glass coverslipping module in the other module receiving region, so that coverslipping both with glass wafers and with tapes is possible using only one apparatus. Alternatively, for example, a glass coverslipping module can also be used in each of the two module receiving regions, or a tape coverslipping module can be used in each of the two module receiving regions; this is useful in particular when the same coverslipping element, i.e. glass wafers or tapes, is to be used, but different coverslipping media are to be employed. Coverslipping with different coverslipping media can thus be accomplished in one apparatus without conversion.

The first and the second module receiving region are, in particular, embodied structurally identically. In particular, the first and the second interface are also structurally identical. This offers the greatest possible exchange capability for the individual coverslipping modules.

The apparatus furthermore has at least one control unit for controlling coverslipping modules received in the first module receiving region and/or in the second module receiving region. Via the first electrical interface, data and/or signals for applying control to a coverslipping module received in the first module receiving region can be transferred to that module. Correspondingly, via the second electronic interface, data and/or signals for controlling a coverslipping module received in the second module receiving region can be transferred to that module.

In a particularly preferred embodiment, via the first and/or the second electrical interface it is also possible to respectively supply power to the coverslipping module received in the respective module receiving region.

Multiple control application programs are, in particular, stored in the control unit, a first control application program for applying control to glass coverslipping modules and a second control application program for applying control to tape coverslipping modules being stored. This is necessary because the glass coverslipping modules and tape coverslipping modules are of different mechanical construction, and control must therefore be applied differently to the individual components for coverslipping the specimen slides.

The control unit is embodied in particular in such a way that it can automatically identify whether a glass coverslipping module or a tape coverslipping module is respectively received in the first module receiving region and/or in the second module receiving region. The control unit then uses the respective control application program provided for the corresponding coverslipping module in order to apply control to that coverslipping module. The control unit thus uses the first control application program when it has detected that a glass coverslipping module is received in a module receiving region, and the second control application program when it has detected that a tape coverslipping module is arranged in a module receiving region. The result of this is that when a glass coverslipping module is exchanged with a tape coverslipping module or vice versa, an operator needs only to exchange the coverslipping modules without having to change any settings.

For automatic identification of the type of coverslipping module of a coverslipping module received in one of the module receiving regions, the control unit in particular reads out a memory element of the received coverslipping module and, as a function of the data read out from the memory element, identifies whether the coverslipping module is a glass coverslipping module or a tape coverslipping module.

The apparatus can encompass in particular an RFID reader for reading RFID transponders of coverslipping modules. By reading the RFID transponders of the coverslipping modules the control unit can then, in particular, identify whether a glass coverslipping module or a tape coverslipping module is involved. In addition, further information regarding the respective coverslipping module, for example a serial number, can also be detected in this manner.

The first interface and/or the second interface each encompass in particular a plug connector for creating a plug connection to a complementarily embodied plug connector of the respective glass coverslipping module or tape coverslipping module that is received in the respective module receiving region. The glass coverslipping module and the tape coverslipping module preferably encompass structurally identical plug connectors, so that they can be attached to the same plug connector of the first electrical interface or of the second electrical interface. The plug connectors are, in particular, arranged in stationary fashion so that the plug connection is created automatically upon insertion of a coverslipping module onto one of the two module receiving regions, and no further intervention is needed in order to plug loose connectors together. Particularly simple handing, and particularly easy exchanging of coverslipping modules, are thereby achieved. Alternatively to the plug connectors, the first electrical interface and/or the second electrical interface can also be embodied in such a way that an electrical contact is created by way of the contact between two flat electrical contact elements.

The first module receiving region and/or the second module receiving region preferably each comprise a support surface for holding a coverslipping module received in the corresponding module receiving region. The received coverslipping module is held in a predetermined position via the contact between said support surface and the respective module, so that particularly simple positioning is achieved. In addition to being supported on the corresponding support surfaces, the coverslipping modules can also be held in the respective module receiving region by way of further fastening devices. In particular, the modules can be held in the module receiving regions by way of a screw connection, clip connection, and/or plug connection that can be nondestructively undone. Orifices having internal threads are provided in the module receiving regions, in particular in their support regions, in order to create screw connections; those surfaces of the coverslipping modules—i.e. of both receivable glass coverslipping modules and receivable tape coverslipping modules—which are supported on the support surfaces likewise comprise orifices at the corresponding locations, so that screws can be threaded through the support surfaces of the coverslipping modules into the orifices of the support surfaces of the apparatus.

In a particularly preferred embodiment, a glass coverslipping module is respectively arranged both in the first receiving region and in the second receiving region. In an alternative embodiment, a tape coverslipping module can be respectively arranged both in the first module receiving region and in the second module receiving region. Alternatively, in a particularly preferred embodiment, a tape coverslipping module is received in the first module receiving region and a glass coverslipping module is received in the second module receiving region, so that with the aid of the apparatus, coverslipping both with tapes and with glass wafers is possible with no need for conversion.

It is furthermore advantageous if the apparatus is constructed in two levels, the two module receiving regions being arranged in an upper level so that they are easily accessible. Furthermore, a quality monitoring module can also be additionally arranged in the upper level; with this module, the coverslipping quality both of specimen slides coverslipped by way of a coverslipping module received in the first module receiving region and of specimen slides coverslipped by way of a coverslipping module received in the second module receiving region can be monitored.

Arranged in the lower level are, in particular, units that are used in shared fashion by both coverslipping modules. In particular, a shared input compartment and a shared output compartment are provided, with which specimen slides, received in racks and intended to be coverslipped both by way of a coverslipping module received in the first module receiving region and by way of a coverslipping module provided in the second module receiving region, can be respectively delivered and removed. In addition, an oven for drying coverslipped specimen slides can also, in particular, be provided in the lower level. The apparatus moreover also has, in particular, a transport unit with which the racks, and thus the specimen slides received in them, can be transported between the individual units of the apparatus.

BRIEF DESCRIPTION OF THE DRAWING VIEWS

Further features and advantages of the invention are evident from the description below, which explains the invention further with reference to exemplifying embodiments in conjunction with the appended Figures, in which.

DETAILED DESCRIPTION OF THE INVENTION

Figure 1:
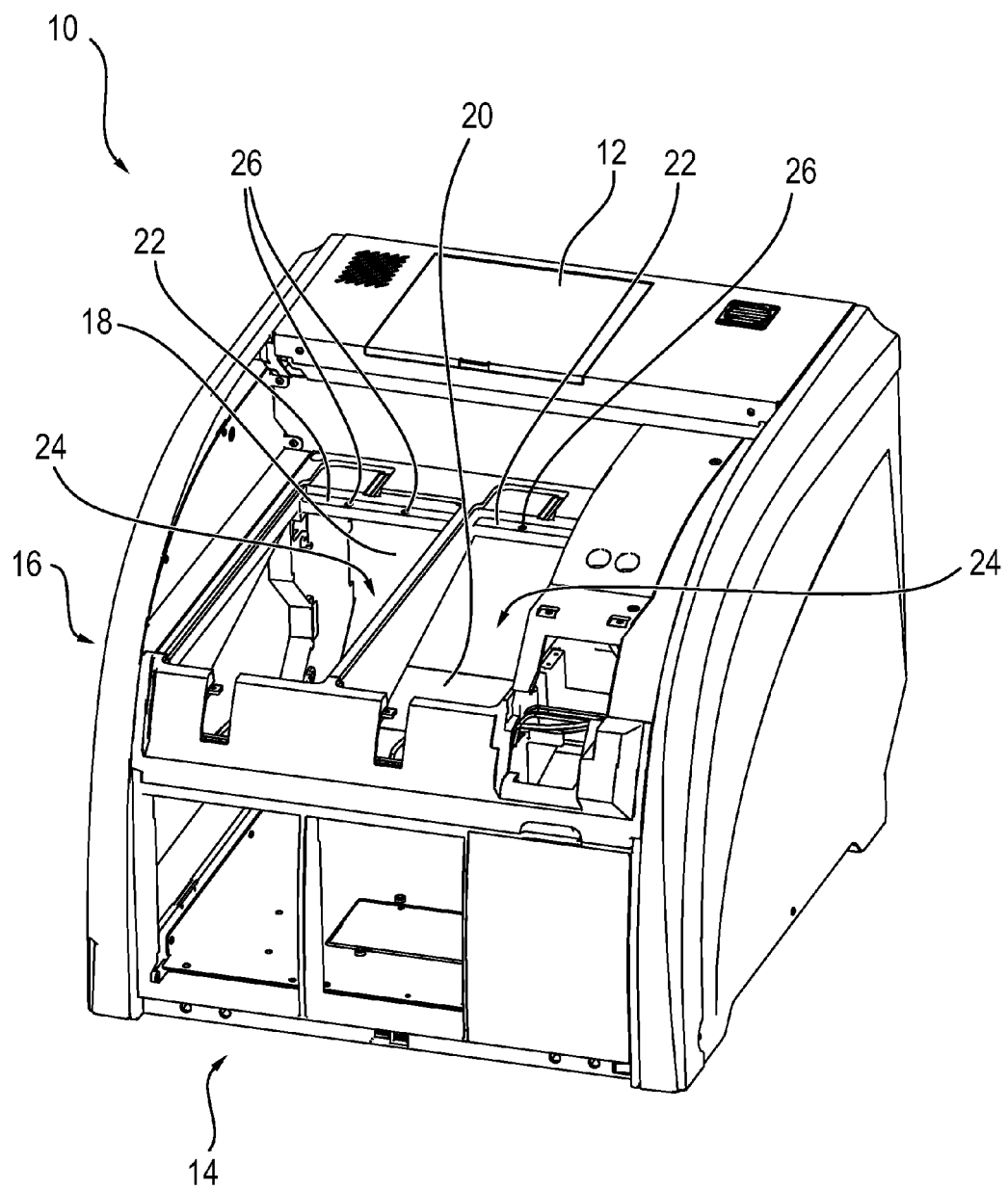
FIG. 1 is a schematic perspective depiction of an apparatus for handling specimen slides, without received coverslipping modules.
Figure 2:
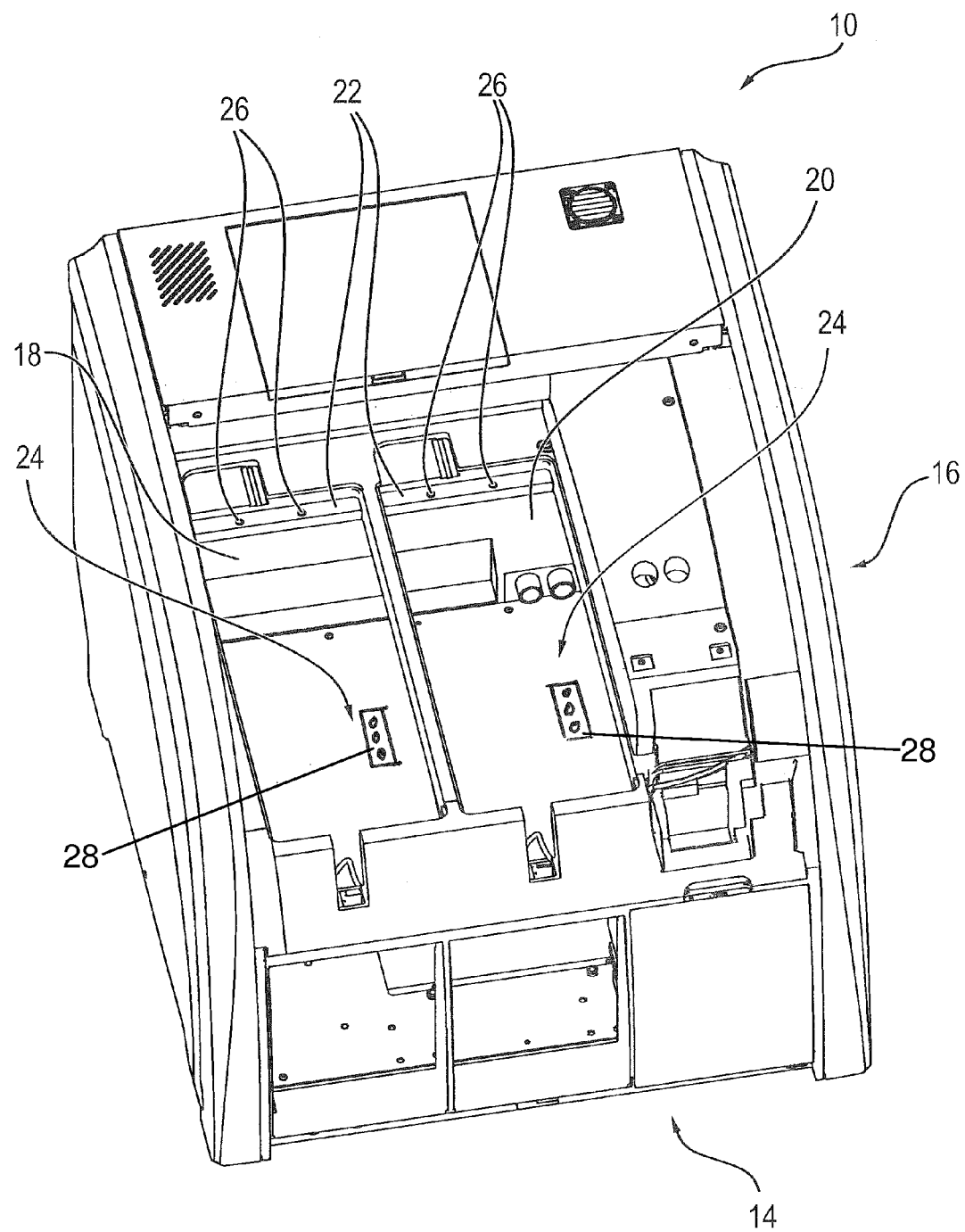
FIG. 2 is a further schematic perspective depiction of the apparatus according to FIG. 1, without received coverslipping modules.

FIGS. 1 and 2 are respective schematic perspective depictions of an apparatus 10 for handling specimen slides, which is also often referred to as a "coverslipping machine." Apparatus 10 encompasses a housing 12 that protects the modules received in apparatus 10. A cover of housing 12 is not depicted here for better visibility of the internally located elements.

Figure 6:
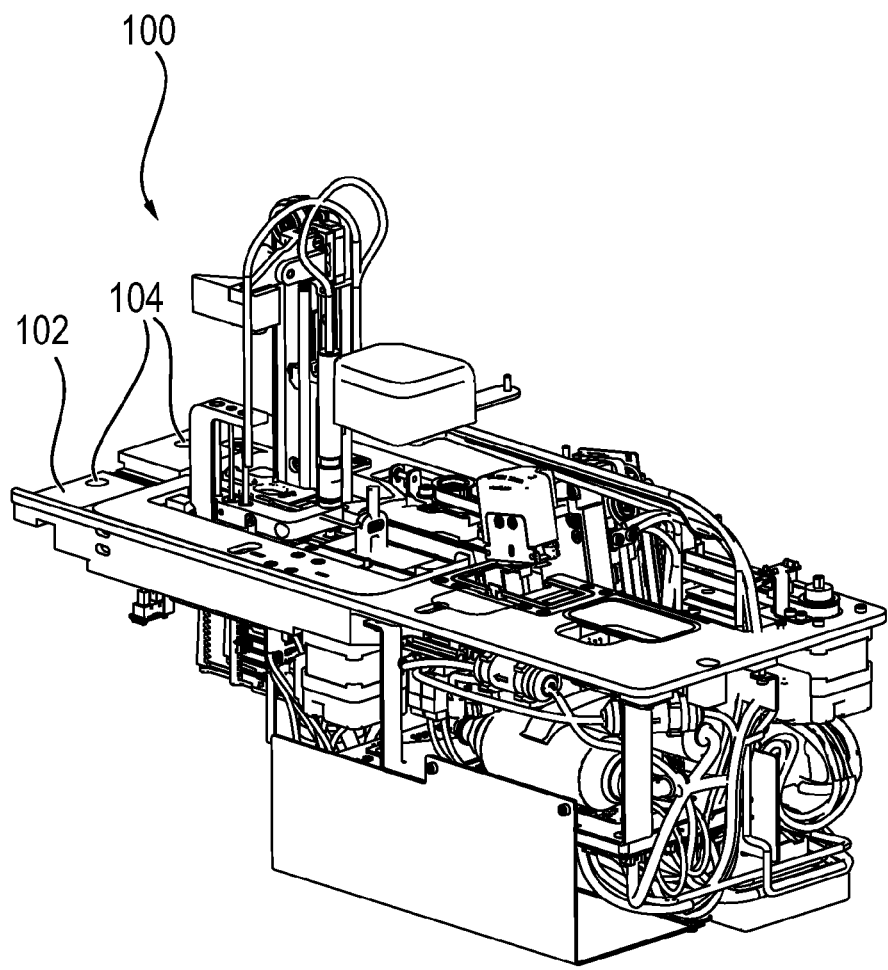
FIG. 6 is a schematic perspective depiction of a glass coverslipping module.
Figure 7:
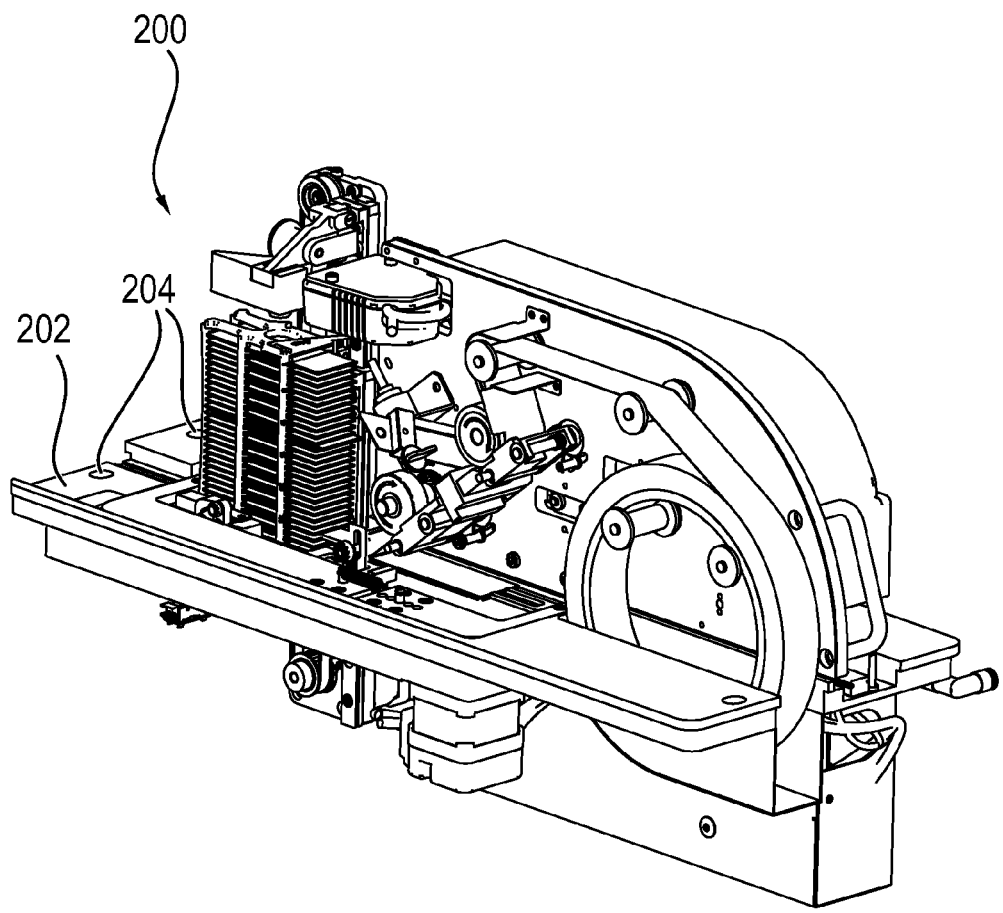
FIG. 7 is a schematic perspective depiction of a tape coverslipping module.

The apparatus is constructed on two levels, a lower level being labeled with the reference character 14 and an upper level with the reference character 16. A first module receiving region 18 and a second module receiving region 20 are provided in upper level 16, and are each embodied in such a way that both a glass coverslipping module 100 for coverslipping specimen slides with glass wafers, and a tape coverslipping module 200 for coverslipping specimen slides with tapes, can be received in them. A glass coverslipping module 100 of this kind is shown in detail in FIG. 6. FIG. 7 depicts a corresponding tape coverslipping module 200.

A quality monitoring module, for monitoring the coverslipping quality of specimen slides coverslipped both by way of a coverslipping module received both in first module receiving region 18 and by way of a coverslipping module received in second module receiving region 20, can also be provided in upper level 16. An input compartment for inputting racks having specimen slides to be coverslipped, an output compartment for outputting coverslipped specimen slides, an oven for drying specimen slides, and a transport unit can be arranged, for example, in lower level 14. All these various units and modules are not depicted in FIGS. 1 and 2 or in the following Figures either, since they are not important for the aspect relevant to the invention and can be embodied in any manner known to one skilled in the art. The construction of apparatus 10 can likewise be different. In particular, the individual modules and units can also be distributed differently onto the two levels 14, 16, or what can be implemented is in fact a construction not in two different levels 14, 16, but instead, for example, in only one level, or also in three levels.

First module receiving region 18 and second module receiving region 20 are, in particular, embodied structurally identically to one another, so that both glass coverslipping modules 100 and tape coverslipping modules 200 can be respectively received in both module receiving regions 18, 20. The construction of such a module receiving region 18, 20 will therefore be explained hereinafter using the example of first module receiving region 18. The corresponding statements are analogously applicable to second module receiving region 20. In an alternative embodiment of the invention, the two module receiving regions 18, 20 can also be configured differently.

Module receiving region 18 comprises a support surface 22 on which a complementary support surface 102 of a glass coverslipping module 100 or a likewise complementary support surface 202 of a tape coverslipping module 200 can be supported when the corresponding coverslipping module 100, 200 is received in first module receiving region 18. Glass coverslipping module 100 and tape coverslipping module 200 are embodied for this purpose in such a way that their support surfaces 102, 202 are identically dimensioned and are each complementary to support surface 22 of first module receiving region 18. Glass coverslipping module 100 and tape coverslipping module 200 can thus easily be exchanged with one another.

Support surface 22 is embodied in particular in such a way that it surrounds on all sides a cutout 24 of first module receiving region 18. What is achieved by way of cutout 24 is that at least some of the components of coverslipping modules 100, 200 can project into the space located therebeneath. The arrangement of a support surface 22 on all sides ensures secure retention of coverslipping module 100, 200 in first module receiving region 18.

Several orifices 26 that each comprise an internal thread are embodied in support surface 22. Support surfaces 102, 202 of coverslipping modules 100, 200 likewise comprise holes 104, 204 at the corresponding locations, so that coverslipping modules 100, 200 can be screwed into place in module receiving regions 18, 20. The result of fastening using screws is that they can easily be loosened again, and coverslipping modules 100, 200 can easily be exchanged. In addition, first module receiving region 18 comprises a first electrical interface (not shown) by way of which a coverslipping module 100, 200 received in first module receiving region 18 can be attached. Second module receiving region 20 correspondingly also comprises a second electrical interface by way of which a coverslipping module 100, 200 that is received in module receiving region 20 can be attached. The two interfaces are, in particularly particular, of identical configuration, so that exchangeability of coverslipping modules 100, 200 is guaranteed. The electrical interfaces can be implemented in particular via plug connections 28. For this, module receiving regions 18, 20 each comprise a first plug connector 28, and coverslipping modules 100, 200 comprise second plug connectors complementary to the first plug connector.

Apparatus 10 furthermore has, in particular, a control unit (not depicted) for applying control to the received coverslipping modules 100, 200. In particular, various control application programs are stored in the control unit, at least one first control application program for applying control to glass coverslipping modules 100, and one second control application program for applying control to tape coverslipping modules 200, being stored. The control unit can, in particular, detect automatically whether a glass coverslipping module 100 or a tape coverslipping module 200 is arranged in the respective module receiving regions 18, 20, and uses the correspondingly associated control application program.

Detection of the respective type of coverslipping module can occur, in particular, via RFID technology. For this, apparatus 100 encompasses in particular at least one RFID reader for reading out RFID transponders arranged on coverslipping modules 100, 200.

As a result of the construction described above, in particular the provision of a mechanical and electrical interface for selectably receiving both glass coverslipping modules 100 and tape coverslipping modules 200, apparatus 10 can easily be converted by the operator of apparatus 10. In particular, the operator can change at any time his or her preference for using a glass coverslipping module 100 or a tape coverslipping module 200 in module receiving regions 18, 20.

Figure 3:
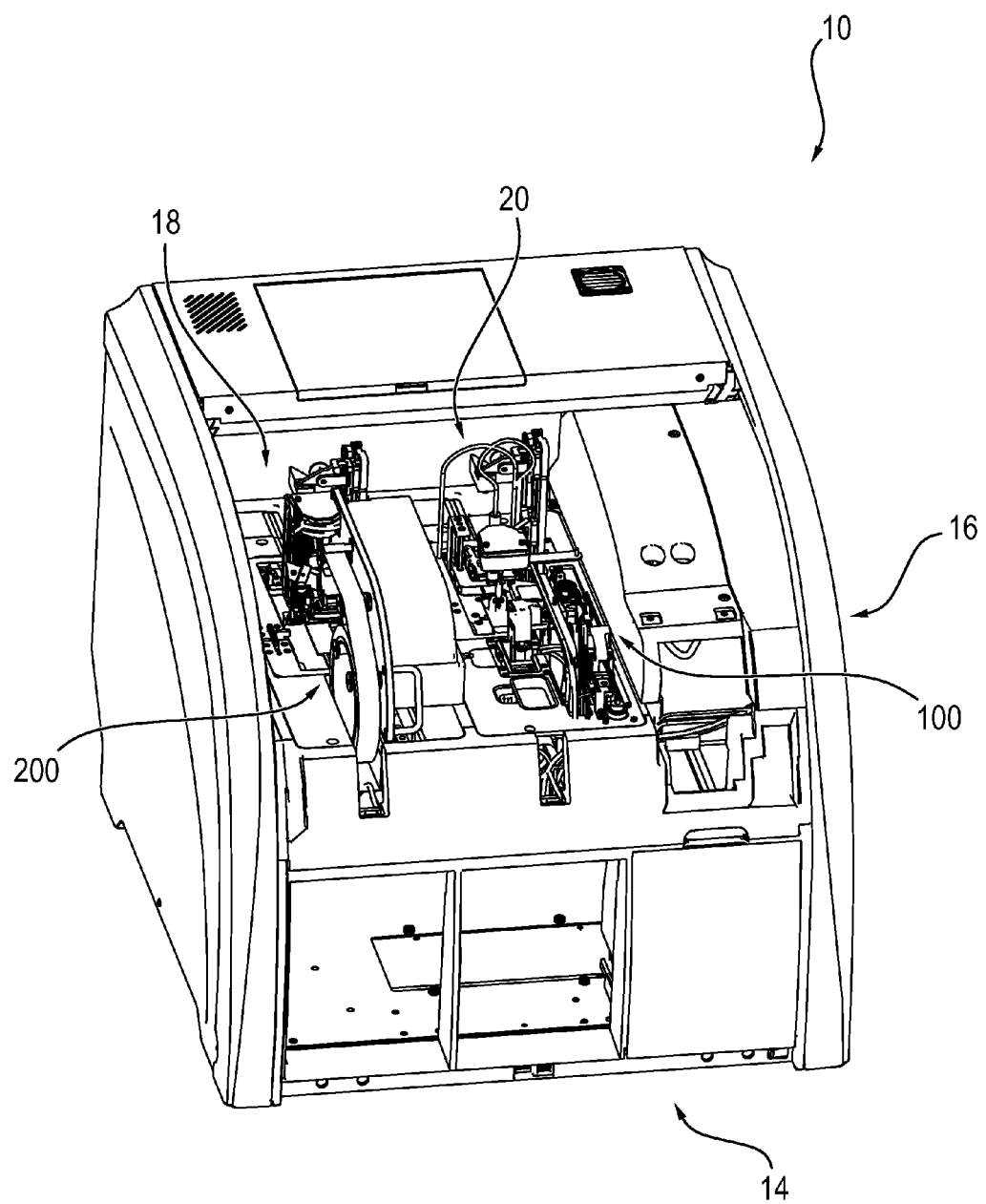
FIG. 3 is a schematic perspective depiction of the apparatus according to FIGS. 1 and 2, a glass coverslipping module being received in one module receiving region and a tape coverslipping module being received in the other module receiving region.

FIG. 3 depicts a particularly preferred first embodiment in which a tape coverslipping module 200 is received in first module receiving region 18, and a glass coverslipping module 100 in second module receiving region 20. The result of this is that coverslipping can occur selectable with tapes or glass wafers using only one apparatus 10, so that no conversion is necessary and quick and effective coverslipping of specimen slides can thus be achieved.

Figure 4:
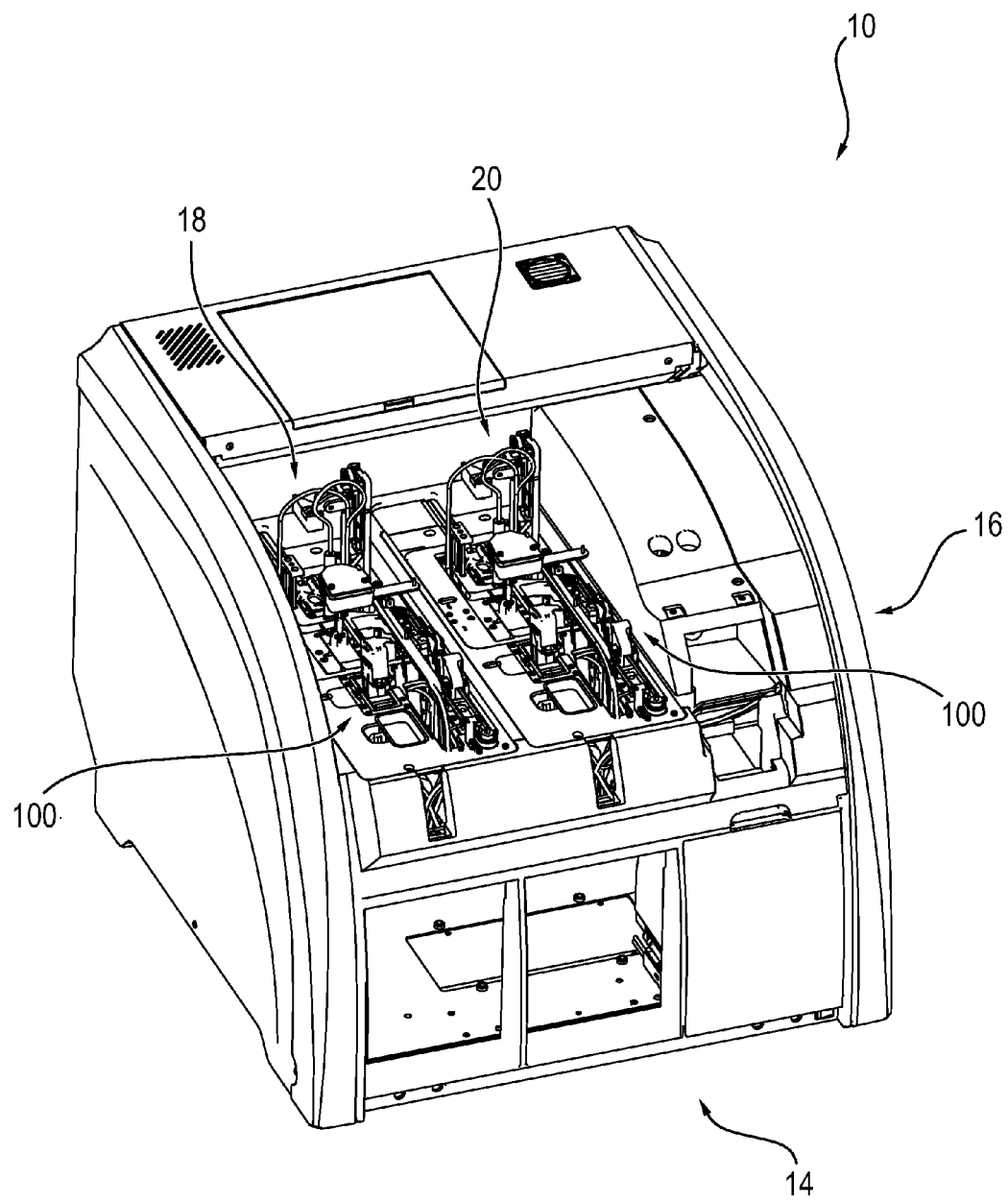
FIG. 4 is a schematic perspective depiction of an apparatus according to FIGS. 1 to 2, a glass coverslipping module being respectively received in both module receiving regions.

FIG. 4 shows a second embodiment in which a glass coverslipping module 100 is respectively arranged in both module receiving regions 18, 20. This can be particularly useful when the specimen slides are all to be coverslipped with glass wafers, but using different coverslipping media. Coverslipping with two different coverslipping media can thus be accomplished, without exchanging the coverslipping medium, by way of the two glass coverslipping modules 100 arranged in module receiving regions 18, 20.

Figure 5:
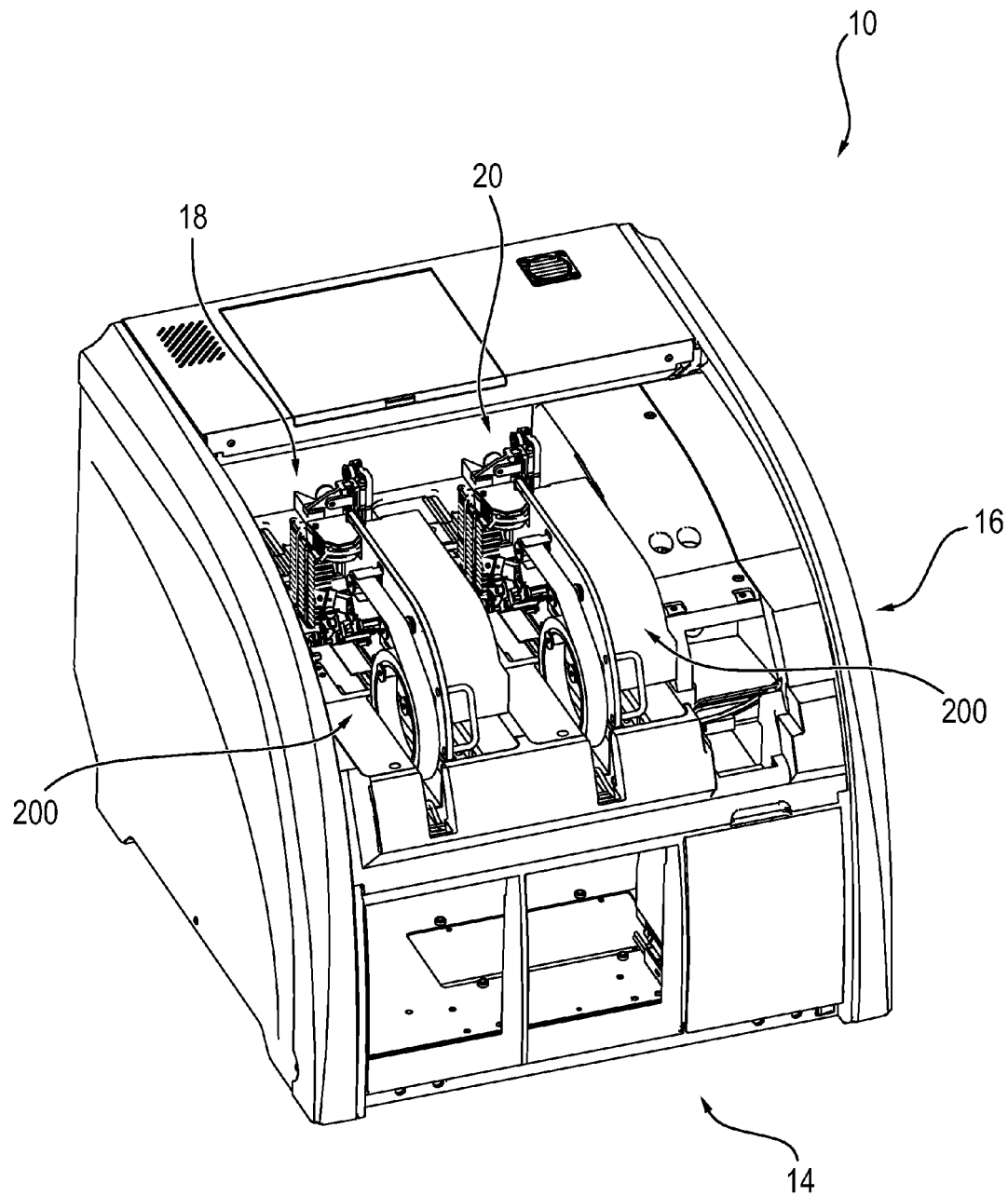
FIG. 5 is a schematic perspective depiction of the apparatus according to FIGS. 1 and 2, a tape coverslipping module being respectively received in both module receiving regions.

In the third embodiment shown in FIG. 5, a tape coverslipping module 200 is arranged respectively in both module receiving regions 18, 20.

Thanks to the simple modular construction, the configuration of apparatus 10 can be varied in particularly simple fashion between these three embodiments with no need for a service person from the company that manufactures apparatus 10.

PARTS LIST

10 Apparatus
12 Housing
14, 16 Level
18, 20 Module receiving regions
22 Support surface
24 Cutout
26 Orifice
28 Plug connector
100 Glass coverslipping module
102 Support surface
104 Hole
200 Tape coverslipping module
202 Support surface
204 Hole

What is claimed is:

1. An apparatus (10) for handling specimen slides, the apparatus comprising:
   a first module receiving region (18) configured to receive a coverslipping module (100, 200) for coverslipping thin sections arranged on the specimen slides with a coverslipping medium and a coverslipping element;
   a first electrical interface in the first module receiving region (18) for attachment of a coverslipping module (100, 200) received by the first module receiving region (18), the first electrical interface being configured for attachment of a glass coverslipping module (100) for coverslipping specimen slides with glass wafers and for attachment of a tape coverslipping module (200) for coverslipping specimen slides with tapes;
   a second module receiving region (20) for receiving a coverslipping module (100, 200) for coverslipping thin sections arranged on specimen slides with a coverslipping medium and a coverslipping element; and
   a second electrical interface in the second module receiving region (20) for attachment of a coverslipping module (100, 200) received by the second module receiving region (20), the second electrical interface being configured for attachment of a glass coverslipping module (100) for coverslipping specimen slides with glass wafers and for attachment of a tape coverslipping module (200) for coverslipping specimen slides with tapes;
   wherein the first module receiving region (18) selectably receives either a tape coverslipping module (200) or a glass coverslipping module (100) and wherein the second module receiving region (20) selectably receives either a tape coverslipping module (200) or a glass coverslipping module (100); and
   wherein the first module receiving region (18) and/or the second module receiving region (20) comprises a support surface (22) for holding a received coverslipping module (100, 200).

2. The apparatus (10) according to claim 1, wherein the first and the second module receiving region (18, 20) are structurally identical.

3. The apparatus (10) according to claim 1, wherein the apparatus (10) comprises a control unit for controlling coverslipping modules (100, 200) received in the first module receiving region (18) and/or in the second module receiving region (20);
   wherein data and/or signals for applying control to a coverslipping module (100, 200) received in the first module receiving region (18) are transferred to such received coverslipping module via the first electrical interface; and
   wherein data and/or signals for applying control to a coverslipping module (100, 200) received in the second module receiving region (20) are transferred to such received coverslipping module via the second electrical interface.

4. The apparatus (10) according to claim 3, wherein data of a first control application program for applying control to glass coverslipping modules (100), and data of a second control application program for applying control to tape coverslipping modules (200), are stored in the control unit;
   wherein the control unit automatically identifies whether a glass coverslipping module (100) or a tape coverslipping module (200) is respectively received in the first module receiving region (18) and/or in the second module receiving region (20); and the control unit uses the respectively associated control application program in order to apply control to the identified coverslipping module.

5. The apparatus (10) according to claim 4, wherein the control unit respectively reads data out from a memory element of a coverslipping module (100, 200) received in the first and/or second module receiving region (18, 20) and, as a function of those read-out data, respectively identifies whether the coverslipping module (100, 200) is a glass coverslipping module (100) or a tape coverslipping module (200).

6. The apparatus (10) according to claim 4, wherein the apparatus (10) comprises an RFID reader for reading RFID transponders of coverslipping modules (100, 200) in order to identify whether the received coverslipping module (100, 200) is a glass coverslipping module (100) or a tape coverslipping module (200).

7. The apparatus (10) according to claim 1, wherein the first electrical interface and/or the second electrical interface includes a plug connector for creating a plug connection to a complementarily embodied plug connector of a respective glass coverslipping module (100) or tape coverslipping module (200).

8. The apparatus (10) according to claim 1, wherein the first module receiving region (18) and/or the second module receiving region (20) comprises at least one orifice (26) having an internal thread for screwing on a received coverslipping module (100, 200).

9. The apparatus (10) according to claim 1, further comprising a glass coverslipping module (100) received in the first module receiving region (18) and another glass coverslipping module (100) received in the second module receiving region (20).

10. The apparatus (10) according to claim 1, further comprising a tape coverslipping module (200) received in the first module receiving region (18) and another tape coverslipping module (200) received in the second module receiving region (20).

11. The apparatus (10) according to claim 1, further comprising a tape coverslipping module (200) received in the first module receiving region (18) and a glass coverslipping module (100) received in the second module receiving region (20).

12. The apparatus (10) according to claim 1, wherein a surface of the received coverslipping module (100, 200) is supported by the support surface (22).

\* \* \* \* \*